(12) United States Patent
Voncken et al.

(10) Patent No.: US 11,506,194 B2
(45) Date of Patent: Nov. 22, 2022

(54) ELECTROSTATIC PERISTALTIC PUMP AND METHOD OF OPERATION

(71) Applicant: KONINKLIJKE PHILIPS N.V., Eindhoven (NL)

(72) Inventors: Rudolf Maria Jozef Voncken, Eindhoven (NL); Johannes Wilhelmus Weekamp, Beek En Donk (NL); Mareike Klee, Straelen (DE); Sergei Shulepov, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 714 days.

(21) Appl. No.: 16/474,298

(22) PCT Filed: Dec. 21, 2017

(86) PCT No.: PCT/EP2017/083967
§ 371 (c)(1),
(2) Date: Jun. 27, 2019

(87) PCT Pub. No.: WO2018/122080
PCT Pub. Date: Jul. 5, 2018

(65) Prior Publication Data
US 2019/0338766 A1    Nov. 7, 2019

Related U.S. Application Data

(60) Provisional application No. 62/440,571, filed on Dec. 30, 2016.

(51) Int. Cl.
*F04B 43/14* (2006.01)
*F04B 45/047* (2006.01)
(Continued)

(52) U.S. Cl.
CPC ............ *F04B 43/14* (2013.01); *F04B 45/047* (2013.01); *F04B 45/10* (2013.01); *F04D 33/00* (2013.01); *A61M 16/0057* (2013.01)

(58) Field of Classification Search
CPC ... A61M 16/0057; F04B 43/14; F04B 45/047; F04B 45/10; F04D 33/00
See application file for complete search history.

(56) References Cited

U.S. PATENT DOCUMENTS

| | | | |
|---|---|---|---|
| 5,192,197 A * | 3/1993 | Culp | F04B 35/04 417/322 |
| 5,705,018 A * | 1/1998 | Hartley | F04B 43/14 216/2 |

(Continued)

FOREIGN PATENT DOCUMENTS

WO    2015042192 A1    3/2015

OTHER PUBLICATIONS

PCT/EP2017/083967 International Search Report dated Mar. 16, 2018.

*Primary Examiner* — Nathan C Zollinger

(57) ABSTRACT

A method of producing a flow of a fluid through a passage (24) defined in a rigid frame (22) comprises selectively actuating a flexible membrane (38) disposed across a midpoint of the passage (24) with an actuating system in a manner which produces a wave-like motion in the membrane (38) thereby causing a peristaltic movement of the fluid through the passage (24).

20 Claims, 12 Drawing Sheets

(51) Int. Cl.
F04B 45/10 (2006.01)
F04D 33/00 (2006.01)
A61M 16/00 (2006.01)

(56) References Cited

U.S. PATENT DOCUMENTS

| | | | | |
|---|---|---|---|---|
| 5,836,750 | A * | 11/1998 | Cabuz | F04B 43/14 |
| | | | | 417/322 |
| 6,007,309 | A * | 12/1999 | Hartley | H02N 1/006 |
| | | | | 417/474 |
| 6,106,245 | A * | 8/2000 | Cabuz | F04B 43/0063 |
| | | | | 417/322 |
| 6,109,888 | A | 8/2000 | Marshall | |
| 7,889,877 | B2 * | 2/2011 | Lutz | F04B 43/12 |
| | | | | 381/191 |
| 11,204,026 | B2 * | 12/2021 | Voncken | F04B 43/04 |
| 2004/0020265 | A1 * | 2/2004 | Cabuz | G01N 33/0011 |
| | | | | 422/90 |

* cited by examiner

| Time | Ctr_m1 | Ctr_m2 | Ctr_m3 | Ctr_m4 | Ctr_t | Ctr_b |
|---|---|---|---|---|---|---|
| $N*T_{period}$ | - | + | + | - | - | + |
| $(N+0.25)*T_{period}$ | + | + | - | - | + | - |
| $(N+0.5)*T_{period}$ | + | - | - | + | - | + |
| $(N+7.5)*T_{period}$ | - | - | + | + | + | - |
| $(N+1)*T_{period}$ | - | + | + | - | - | + |

FIG. 13

| Time | Ctr_m1 | Ctr_m2 | Ctr_m3 | Ctr_m4 | Ctr_t | Ctr_b |
|---|---|---|---|---|---|---|
| $N*T_{period}$ | - | + | + | - | - | + |
| $(N+0.25)*T_{period}$ | - | - | + | + | - | + |
| $(N+0.5)*T_{period}$ | + | - | - | + | - | + |
| $(N+7.5)*T_{period}$ | + | + | - | - | - | + |
| $(N+1)*T_{period}$ | + | - | - | + | + | - |
| $(N+1.25)*T_{period}$ | + | + | - | - | + | - |
| $(N+1.5)*T_{period}$ | - | + | + | - | + | - |
| $(N+1.75)*T_{period}$ | - | - | + | + | + | - |
| $(N+2)*T_{period}$ | - | + | + | - | - | + |
| $(N+2.25)*T_{period}$ | - | - | + | + | - | + |
| $(N+2.5)*T_{period}$ | + | - | - | + | - | + |
| $(N+2.75)*T_{period}$ | + | + | - | - | - | + |
| $(N+3)*T_{period}$ | + | - | - | + | + | - |

FIG. 14

ELECTROSTATIC PERISTALTIC PUMP AND METHOD OF OPERATION

This application is the U.S. National Phase application under 35 U.S.C. § 371 of International Application No. PCT/EP2017/083967, filed on Dec. 21, 2017 and U.S. Provisional Application No. 62/440,571, filed Dec. 30, 2016. These applications are hereby incorporated by reference herein.

BACKGROUND OF THE INVENTION

1. Field of the Invention

The present invention pertains apparatuses for producing a flow of gas. More particularly, the present invention pertains to apparatuses which generate a flow of gas via a peristaltic motion. The present invention also pertains to systems which generate a flow of gas via peristaltic motion. The present invention further pertains to methods of generating a flow of gas by creating a peristaltic motion via application of electrostatic forces. The present invention also pertains to methods of manufacturing an apparatus for use in generating a flow of gas via a peristaltic motion.

2. Description of the Related Art

There exists many different types of pumps for different types (i.e., liquid, gas) of fluids. The optimal pump type for an application depends on the requirements of the particular application. Typically, the main requirements of a particular application are the required pressure and flow rate of the pump. Other possible requirements are maximum weight, geometrical dimensions, cost, sound level, required efficiency, reliability and lifetime of the pump and/or related components.

For example, for an application in continuous positive airway pressure therapy (CPAP therapy, for treating sleep apnea patients) with moderate pressure levels (e.g., without limitation, about 0.04 Bar) and high flow rates (e.g., without limitation, about 100 liter/min), radial blowers are typically preferred because they can fulfill the flow rate and pressure requirements even though such devices are typically quite bulky and produce a lot of noise due to the high rotational operating speeds and high amount of turbulence resulting from their basic operating principles.

Given certain dimensions of the desired outflow, an ideal pump system, with respect to efficiency and pump dimensions, which is adaptable to provide a required pressure level and flow rate, will look roughly like pump system 10 as shown in FIG. 1 (without specifying the mechanism for pressurizing the fluid). The cross-flow dimensions of pump 12 can be dimensioned in perfect fit with the desired outflow dimensions, thus allowing for the velocity of the fluid (shown by arrows 14) in pump 12 to be almost equal to those in the outflow (due to compressibility and conservation of mass the velocity will slightly decrease). Maintaining a nearly constant velocity is desirable as significant changes in velocity typically cause turbulence and loss of efficiency and thus are generally undesirable. In such an "ideal" arrangement, the whole volume of pump 12 is utilized for pressurizing the fluid (as shown by vertical lines with horizontal spacing decreasing as pressure of the fluid increases) passing therethrough which enables an optimal use of the pump volume and enables minimal dimensions.

SUMMARY OF THE INVENTION

As one aspect of the invention, a method of producing a flow of a fluid through a passage defined in a rigid frame is provided. The method comprises: selectively actuating a flexible membrane disposed across a midpoint of the passage with an actuating system in a manner which produces a wave-like motion in the membrane thereby causing a peristaltic movement of the fluid through the passage.

Selectively actuating the flexible membrane may comprise moving portions of the membrane in a direction perpendicular to a longitudinal central axis of the passage.

The membrane may comprises a conductive material and selectively actuating the flexible membrane may comprise attracting portions of the membrane toward one of an upper portion of the passage or toward a lower portion of the passage via an electrostatic force.

The actuating system may comprise: a number of upper electrodes disposed adjacent an upper portion of the passage; a number of lower electrodes disposed adjacent a lower portion of the passage; and a single membrane electrode disposed in or on the membrane; and selectively actuating the membrane may comprise attracting portions of the membrane toward either the upper portion of the passage or toward the lower portion of the passage via an electrostatic force by: electrically connecting the single membrane electrode to ground; selectively electrically connecting an upper electrode to a positive voltage; and selectively electrically connecting a lower electrode to a negative voltage.

The actuating system may comprise: a number of upper electrodes disposed adjacent an upper portion of the passage; a number of lower electrodes disposed adjacent a lower portion of the passage; and a number of membrane electrodes disposed in or on the membrane; and selectively actuating the membrane may comprise attracting portions of the membrane toward either the upper portion of the passage or toward the lower portion of the passage via an electrostatic force by: selectively electrically connecting the number of membrane electrodes to either a positive voltage or a negative voltage; selectively electrically connecting at least one of the upper electrodes to a positive voltage; and selectively electrically connecting at least one of the lower electrodes to a negative voltage.

The actuating system may comprise: a plurality of upper electrodes disposed adjacent an upper portion of the passage; a plurality of lower electrodes disposed adjacent a lower portion of the passage; and a single membrane electrode disposed in or on the membrane; and selectively actuating the membrane may comprise attracting portions of the membrane toward either the upper portion of the passage or toward the lower portion of the passage via an electrostatic force by: electrically connecting the single membrane electrode to ground; selectively electrically connecting at least one of the upper electrodes to a positive voltage; and selectively electrically connecting at least one of the lower electrodes to a negative voltage.

Selectively actuating the membrane may further comprise: selectively electrically connecting at least another one of the upper electrodes to a negative voltage; and selectively electrically connecting at least another one of the lower electrodes to a positive voltage.

The actuating system may comprise: a plurality of upper electrodes disposed adjacent an upper portion of the passage; a plurality of lower electrodes disposed adjacent a lower portion of the passage; and a single membrane electrode disposed in or on the membrane; and selectively actuating the membrane may comprise attracting portions of the membrane toward either the upper portion of the passage or toward the lower portion of the passage via an electrostatic force by: selectively electrically connecting the single membrane electrode to either a positive voltage or a negative voltage; selectively electrically connecting at least one of the upper electrodes to a positive voltage; and selectively electrically connecting at least one of the lower electrodes to a negative voltage.

Selectively actuating the membrane may further comprise: selectively electrically connecting at least another one of the upper electrodes to a negative voltage; and selectively electrically connecting at least another one of the lower electrodes to a positive voltage.

The actuating system may comprise: a single upper electrode disposed adjacent an upper portion of the passage; a single lower electrode disposed adjacent a lower portion of the passage; and a plurality of membrane electrodes disposed in or on the membrane; and selectively actuating the membrane may comprise attracting portions of the membrane toward either the upper portion of the passage or toward the lower portion of the passage via an electrostatic force by: selectively electrically connecting at least one of the membrane electrodes to a positive voltage; selectively electrically connecting the single upper electrode to one selected from the group consisting of a positive voltage and a negative voltage; and selectively electrically connecting the single lower electrode to the other one in the group.

Selectively actuating membrane may further comprise selectively electrically coupling another one of the membrane electrodes to a negative voltage.

The actuating system may comprise: a number of upper electrodes disposed adjacent an upper portion of the passage; a number of lower electrodes disposed adjacent a lower portion of the passage; and a single membrane electrode disposed in or on the membrane; and selectively actuating the membrane may comprise attracting portions of the membrane toward either the upper portion of the passage or toward the lower portion of the passage via an electrostatic force by: electrically connecting the single membrane to a first potential; electrically connecting at least one of an upper electrode or a lower electrode to a second potential different than the first potential.

The actuating system may comprise: a single upper electrode disposed adjacent an upper portion of the passage; a single lower electrode disposed adjacent a lower portion of the passage; and a plurality of membrane electrodes disposed in or on the membrane; and selectively actuating the membrane may comprise attracting portions of the membrane toward either the upper portion of the passage or toward the lower portion of the passage via an electrostatic force by: electrically connecting the single upper electrode to a first potential; electrically connecting the single lower electrode to a second potential different than the first potential; and electrically connecting at least one of the membrane electrodes to a third potential different from at least one of the first potential and the second potential.

Selectively actuating the membrane may further comprise electrically connecting at least one of the membrane electrodes to a fourth potential different from at least one of the first potential and the second potential.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 13 and 14 show switching sequences according to example embodiments of the invention for an apparatus such as shown in FIG. 10;

DETAILED DESCRIPTION OF EXEMPLARY EMBODIMENTS

Figure 1:
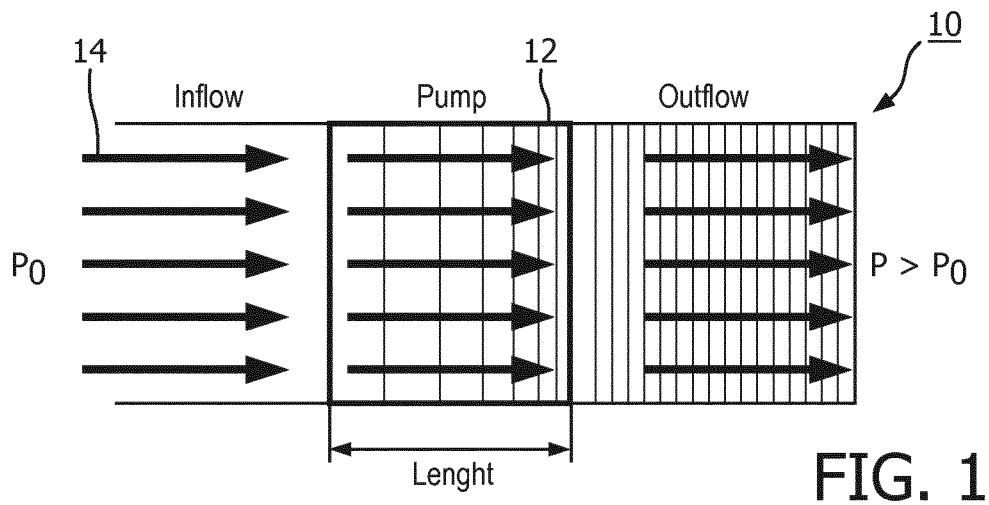
FIG. 1 is a schematic representation of a theoretical ideal pump system.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other. As used herein, "fixedly coupled" or "fixed" means that two components are coupled so as to move as one while maintaining a constant orientation relative to each other.

As used herein, "about" in a phrase such as "disposed about [an element, point or axis]" or "extend about [an element, point or axis]" or "[X] degrees about an [an element, point or axis]," means encircle, extend around, or measured around. When used in reference to a measurement or in a similar manner, "about" means "approximately," i.e., in an approximate range relevant to the measurement as would be understood by one of ordinary skill in the art.

As used herein, "generally" means "in a general manner" relevant to the term being modified as would be understood by one of ordinary skill in the art.

As used herein, "substantially" means for the most part, by a large amount or degree, as would be understood by one of ordinary skill in the art. Thus, for example, a first element "substantially" disposed in a second element is, for the most part, disposed in the second element.

As used herein, the word "unitary" means a component is created as a single piece or unit. That is, a component that includes pieces that are created separately and then coupled together as a unit is not a "unitary" component or body.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

As used herein, the phrase "sealingly engage" shall mean elements which contact each other in a manner such that a generally air-tight seal is formed therebetween.

As used herein, the term "controller" shall mean a programmable analog and/or digital device (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

It will be appreciated from the following description that embodiments of the present invention utilize electrostatic forces to create a peristaltic pumping action in a pumping apparatus which functions closer to the ideal pump discussed in regard to FIG. 1 than conventional solutions.

Figure 2:
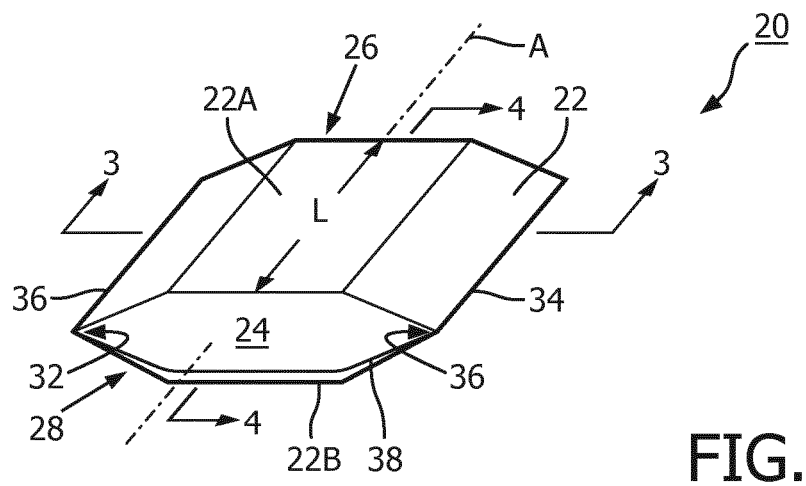
FIG. 2 is a partially schematic isometric view of a pumping apparatus according to one example embodiment of the invention.
Figure 3:
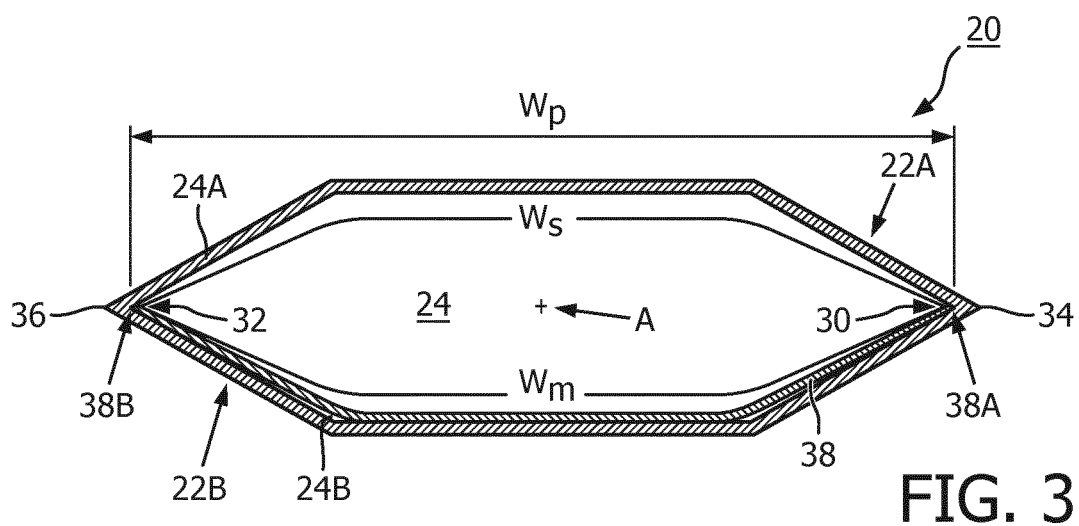
FIG. 3 is a partially schematic sectional view of the pumping apparatus of FIG. 2 taken along line 3-3 of FIG. 2 and viewed along the longitudinal central axis of the apparatus.

FIGS. 2, 3, 4A and 4B show an example of a pumping apparatus 20 for generating a flow of gas in accordance with an exemplary embodiment of the present invention. Pumping apparatus 20 includes a frame 22 having a passage 24 defined therethrough. Passage 24 is of a generally uniform cross-section and extends along a longitudinal central axis A thereof a length L between an inlet 26 and an outlet 28 and is generally structured such that any fluid entering inlet 26 can only exit via outlet 28. In the example embodiment of the present invention illustrated in FIGS. 2, 3, 4A and 4B, passage 24 has a hexagonal cross-sectional shape, however, it is to be appreciated that other cross-sectional shapes may be employed without varying from the scope of the present invention. Passage 24 has a first side 30 and a second side 32 disposed opposite first side 30. Passage 24 has a maximum width $w_p$ as measured between a midline 34 of first side 30 and a midline 36 of second side 32. Passage 24 is generally separated into two sub-portions, i.e., an upper portion 24A and a lower portion 24B, via a flexible pumping membrane 38 positioned within passage 24. More particularly, pumping membrane 38 is generally coupled at a first edge 38A thereof to first side 30 of passage 24 at midline 34 thereof and is coupled at a second edge 38B, disposed opposite first edge 38A, to second side 32 of passage 24 at midline 36 thereof. Accordingly, pumping membrane 38 generally segregates the bounds (i.e., frame 22) of passage 24 into an upper frame portion 22A and a lower frame portion 22B. Passage 24 has a maximum height H which is the distance between a central portion (not numbered) of upper frame portion 22A and a central portion of lower frame portion 22B. As will be discussed in further detail below, because the strength of electro-static attraction heavily depends on the applied voltage and distance between electrode and pumping foil, for practical voltages (several hundreds of Volt), passage height H is generally limited to dimensions in the order of magnitude of 0.1-0.5 mm. Pumping membrane 38 has an actual width $w_m$, as measured along pumping membrane 38 between first edge 38A and second edge 38B, which is greater than width $w_p$ of passage 24, and which is generally equal to the actual width $w_s$ as measured along the upper (or lower) surface of passage 24. In other words, if pumping membrane 38 were laid flat, the distance between first edge 38A and second edge 38B would be the actual width $w_m$ of membrane 38. Accordingly, pumping membrane 38 typically assumes a resting position such as shown in FIG. 3 when not acted upon by electrostatic forces, as will be described in further detail elsewhere herein, and can generally be sealingly engaged with either of the upper or lower surfaces of passage 24 due to its actual width $w_m$ being generally equal to the width $w_s$ of either of the upper or lower surfaces (not numbered) of passage 24.

Figure 4A:
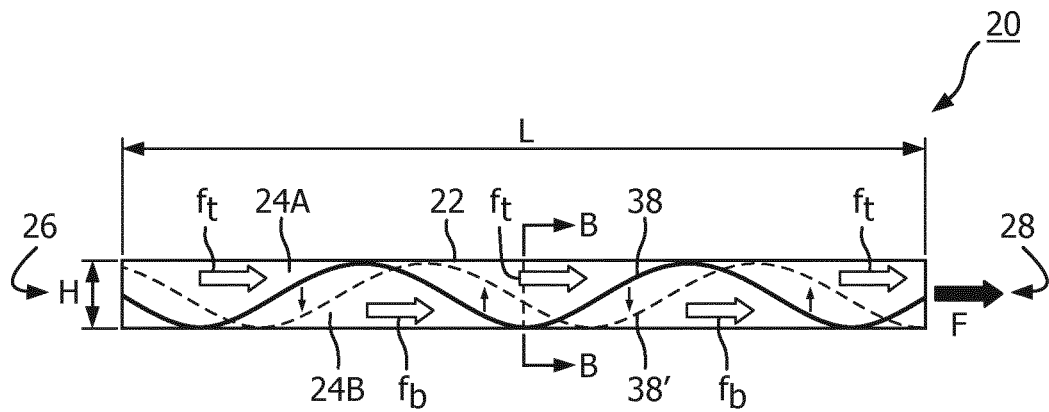
FIG. 4A is a partially schematic sectional view of the pumping apparatus of FIG. 2 taken along line 4-4 of FIG. 2 showing the pumping membrane disposed in positions corresponding to a peristaltic movement.
Figure 4B:
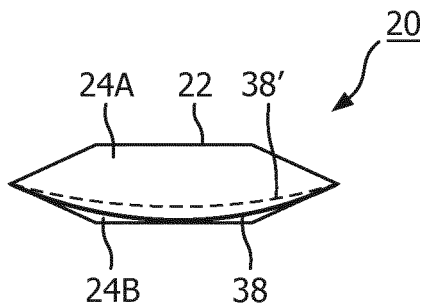
FIG. 4B is a partially schematic sectional view of the arrangement of FIG. 4A taken along line B-B of FIG. 4A.

FIG. 4A, which shows a sectional view of pumping apparatus 20 taken along line 4-4 of FIG. 2, and FIG. 4B, which shows a sectional view of pumping apparatus 20 taken along line B-B of FIG. 4A, provide schematic illustrations of how a flow F of gas may be produced using pumping apparatus 20. More particularly, a wave-like motion may be produced in pumping membrane 38 by selectively moving different portions thereof vertically in either an upward or downward direction such as shown by the small arrows in FIGS. 4A and 4B. By moving pumping membrane 38 in the direction of the small arrows, the wave-like shape of pumping membrane 38 is transitioned toward the alternately positioned wave-like shape 38' shown in dashed line in FIGS. 4A and 4B. By further transitioning the wave along the length L of passage 24 from inlet 26 to outlet 28, pockets of air, as generally denoted by the larger arrows $f_t$ and $f_b$ in FIG. 4A, are transitioned along both upper portion 24A and lower portion 24B, respectively, of passage 24 in a peristaltic manner. Hence, it is to be appreciated that generally half the total flow F through passage 24 is from flow $f_t$ which flows through upper portion 24A and generally half the total flow F through passage 24 is from flow $f_b$ which flows through lower portion 24B. As the frequency of the waves produced in membrane 38 is increased, so too is the velocity of the flow passing through passage 24. The length of the waves produced in membrane 38 may be varied to affect pressure.

Figure 5:
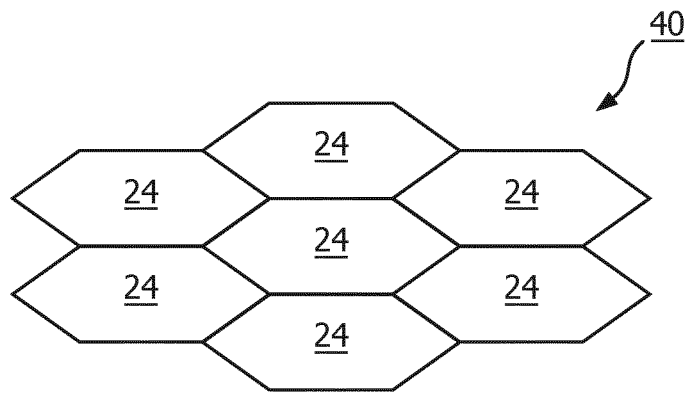
FIG. 5 is a partially schematic sectional view of a plurality of apparatuses such as shown in FIG. 2 arranged in accordance with an example of the present invention.

By combining several passages 24 in a honeycomb-like structure, the cross-flow dimensions of such an arrangement can be nearly perfectly adapted to the required outflow dimensions of a particular application. FIG. 5 shows an example of such a structure in which seven passages 24 (shown with pumping membrane 38 omitted) have been arranged in a honeycomb-like pumping apparatus structure 40. It is to be appreciated that such pattern can be repeated as many times as needed to fulfill the pump requirements of a particular application. As each passage 24 is of very small dimensions, such honeycomb structure can be generally fabricated using thin films (e.g., typical range 2-15 µm in thickness) which are layered together and subsequently expanded, as will be discussed in further detail below.

Figure 6:
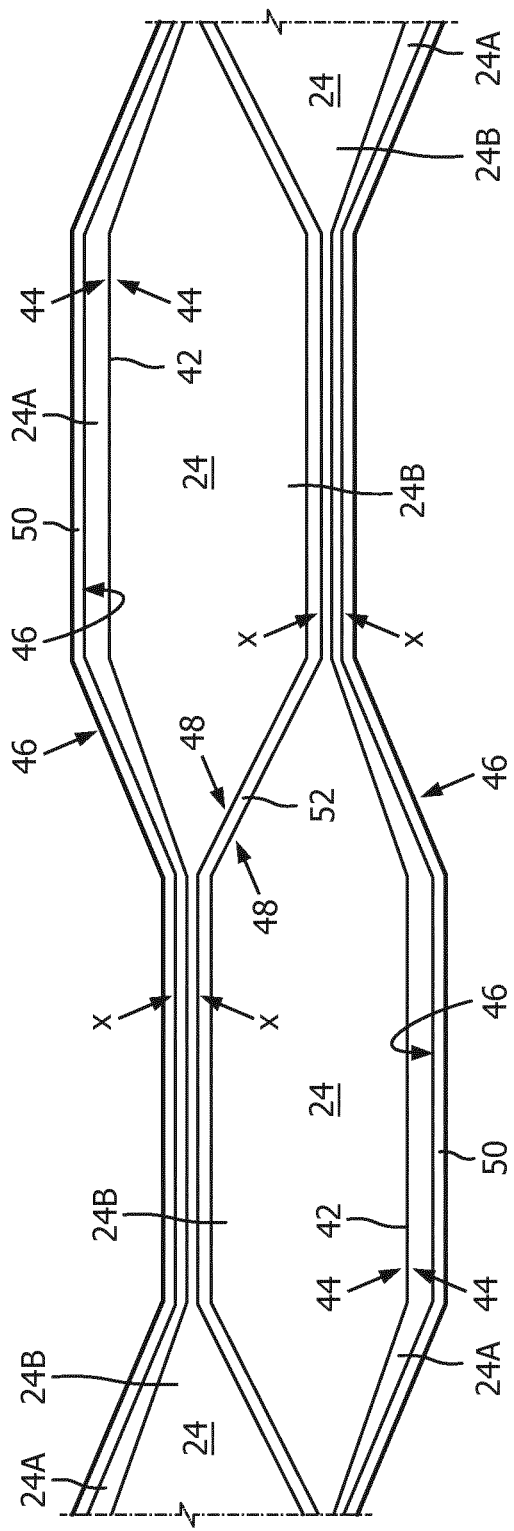
FIG. 6 is a partially schematic detail sectional view of a portion of the arrangement of FIG. 5.

In order to actuate each pumping membrane 38 against fluid pressure differences in the manner as discussed in conjunction with FIGS. 4A and 4B, pumping apparatus 20 further includes an actuating system which is structured to selectively move portions of pumping membrane 38 either upward toward upper portion 22A or downward toward lower portion 22B of each passage 24 in a manner which produces the peristaltic wave-like movement in pumping membrane 38. The mechanism utilized to actuate pumping membrane 38 against the fluid pressure difference in embodiments described herein is an alternating (with time) electro-static attraction of pumping membrane 38 by either upper portion 22A or lower portion 22B of frame 22. For this purpose, the honeycomb structure 40 (which equates to the frame 22 previously discussed in regard to a single passage) of FIG. 5 may be formed from structural films (e.g., without limitation, PET of polypropylene foil with thickness of several microns (e.g. 10 µm)). Such structural films can be plated on one or both sides with metal electrodes to which alternating voltages may be applied. In order for electrostatic attraction to occur, pumping membrane 38 is also formed, in whole or in-part, by plated structural film (comparable to the honeycomb structure 40) or a conductive (e.g., metal) film. In order to avoid short circuiting in the resulting arrangement, the conductive material on the structural films or the pumping membrane must be isolated from each other. Such isolation can be accomplished in several ways. One example arrangement is illustrated in FIG. 6, wherein a pumping membrane 38 includes a metal film 42 which is coated on both sides with a dielectric 44. In such arrangement, dielectric 44 isolates metal film 42 of pumping membrane from metal layers 46 and 48, which are disposed on structural films 50 and 52, respectively.

Continuing to refer to FIG. 6, when a (positive or negative) voltage is applied to metal layers 46, and metal films 42 are connected to ground, metal films 42, and thus pumping membranes 38, are attracted toward metal layers 46 (such as shown in the figure) due to the potential difference. When the voltage is removed from metal layers 46 (which are then connected to ground) and is instead applied to metal layers 48, metal films 42, and thus pumping membranes 38, will be attracted toward the opposite side of passages 24. From such example arrangement, it can be readily appreciated that by applying the same voltage to metal layers on both sides of either structural films 50 or structural film 52 (but not both), in a given cross-section, half of the pumping membranes 38 will be moving upward and half of the pumping membranes 38 will be moving downward, thus giving a better dynamic balancing than a situation wherein all pumping membranes 38 would be moving in the same direction in a given cross-section. In another example arrangement (not shown), a dielectric coating is applied on metal layers 46 and 48 instead of on metal film(s) 42.

Figure 7:
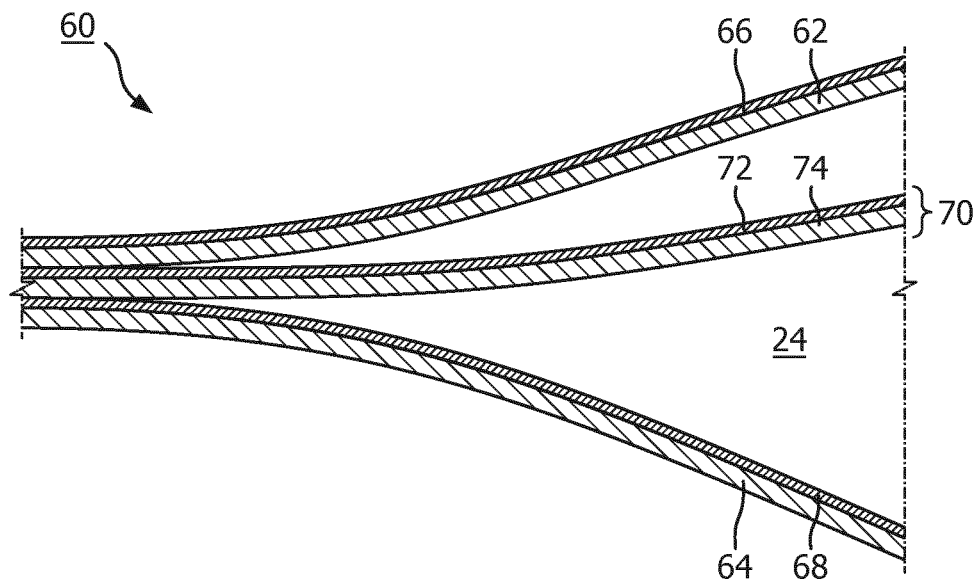
FIGS. 7 and 8 are sectional views of portions of pumping apparatus according to example embodiments of the invention.
Figure 8:
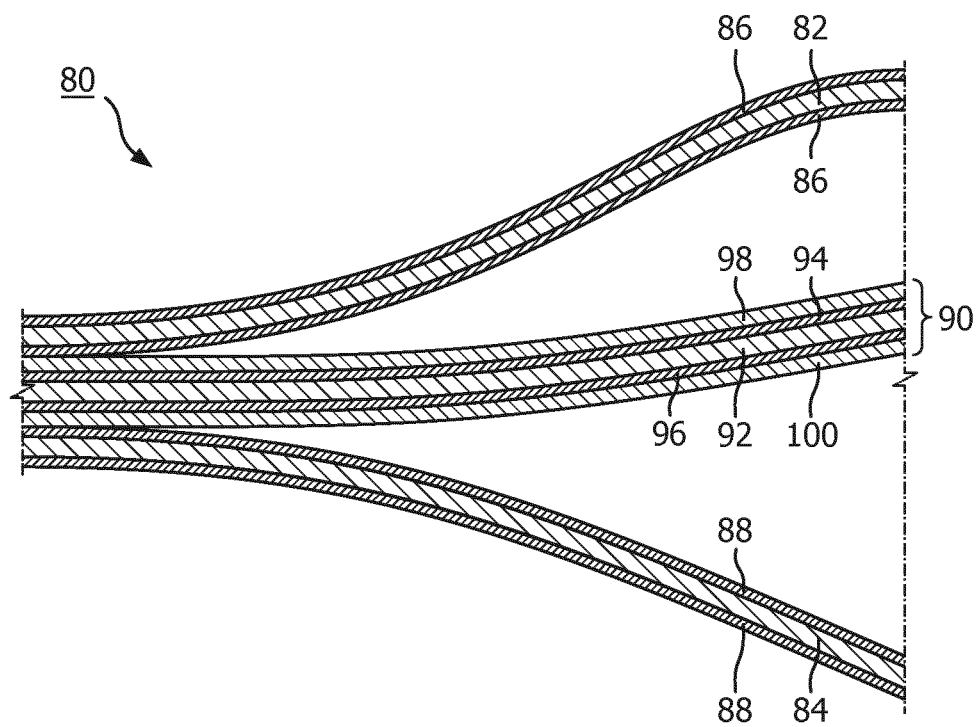

FIGS. 7 and 8 show portions of further alternative honeycomb structures 60, 80 in accordance with example embodiments of the present invention. Referring to FIG. 7, a portion of an example structure 60 is illustrated wherein each of an upper structural film 62 and a lower structural film 64 are coated, respectively, with a metal layer 66, 68 only on the upper surfaces thereof. In such arrangement, a pumping membrane 70 includes a structural film 74 with a metal layer 72 disposed on the upper surface thereof. As the metal layers 66, 72 and 68 are all disposed above non-conductive layers (i.e., layers 62, 74, 64) such conductive layers 66, 72 and 68 are isolated from each other using a minimal amount of layers.

In contrast to the minimal arrangement of FIG. 7, FIG. 8 illustrates a portion of an example structure 80 wherein each of an upper structural film 82 and a lower structural film 84 are coated with a metal layer 86, 88 on both the upper and lower surfaces thereof. In such arrangement, a pumping membrane 90 includes a non-conductive central core layer 92 having metal film layers 94 and 96 disposed on the upper and lower surfaces thereof. The surfaces of metal film layers 94 and 96 opposite central core layer 92 have a dielectric coating 98, 100 disposed thereon which serves to isolate metal layer 86 from metal layer 94 and metal layer 88 from metal layer 96.

It is to be appreciated that the embodiments show in FIGS. 7 and 8 are provided for example purposes only, and that other suitable variations of layered arrangements not particularly described herein may also be employed without varying from the scope of the invention.

Figure 9:
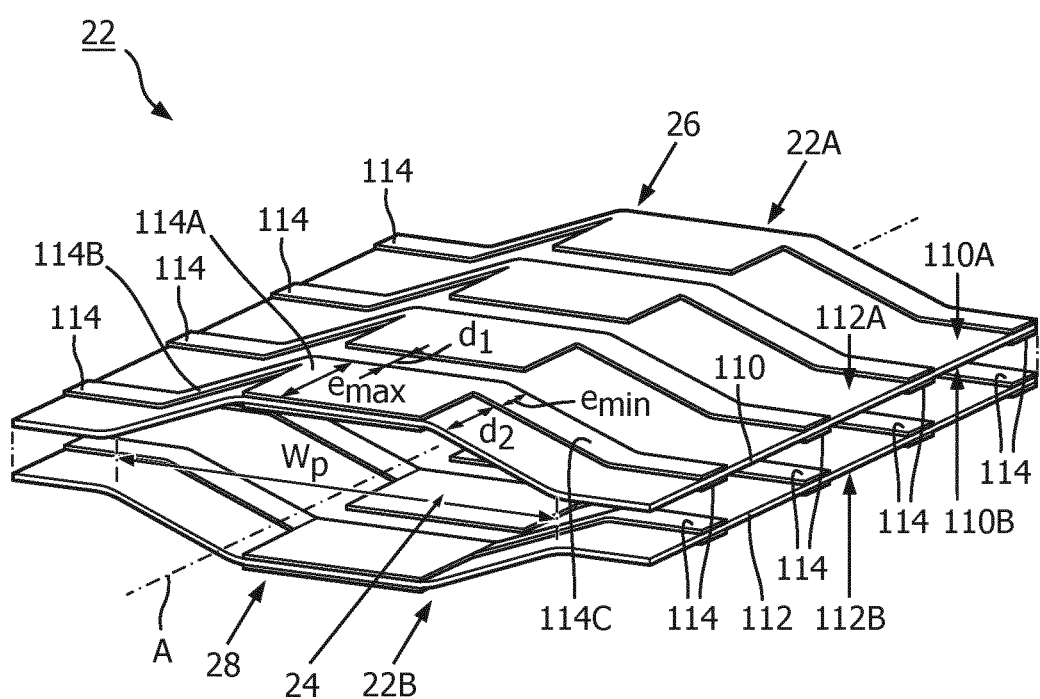
FIG. 9 is a partially exploded view of a portion of an apparatus according to an example embodiment of the invention.

In order to make the direction of electrostatic attraction dependent on the length positioning in passage 24, the metal plating is patterned in a manner such that conductive lines which serve as electrodes are made in the direction perpendicular to longitudinal axis A of each passage 24. Such electrodes are spaced in the longitudinal direction of passage 24 in a manner which makes it possible to apply different voltages at different positions on the top (e.g., upper portion 22A of frame 22) or the bottom (e.g., lower portion 22B of frame 22) of passage 24, depending on the length position of the respective electrode relative to passage 24. An example embodiment of such a patterned arrangement is illustrated in FIG. 9 which generally shows an isometric view of a frame 22 of an apparatus 20 (such as previously described in conjunction with FIGS. 2, 3, 4A and 4B) exploded into an upper portion 22A and a lower portion 22B. Similar to the arrangement shown in FIG. 8, each of upper portion 22A and lower portion 22B includes a structural film 110, 112 with a metal layer (not numbered) disposed on both an upper surface 110A, 112A and a lower surface 110B, 112B thereof (only upper surfaces 110A and 112A of structural films 110 and 112 are visible in FIG. 9, however, it is to be understood that lower surfaces 110B and 112B are each patterned in the same manner as upper surfaces 110A and 112A and thus will not be described in particular detail herein). Each metal layer is patterned so as to form a plurality (four are shown) of spaced (by a minimum distance $d_1$) conductors 114 on both upper and lower surfaces 110A, 112A and 110B, 112B of structural films 110 and 112. Each conductor 114 extends generally perpendicularly with respect to central longitudinal axis A of passage 24. There are however several precise geometries possible in order to optimize the peristaltic motion of the pumping foil. An example of one such geometry is described below. In the example embodiments described herein, the general arrangement of all of electrodes 114 is generally the same and thus only the arrangement of electrodes 114 disposed on upper surface 110A of structural film 110 is discussed in detail herein.

Each electrode 114 has a width (as measured in the longitudinal direction of passage) which may be selectively varied. In the example illustrated in FIG. 9, the width of each electrode 114 varies from a maximum electrode width $e_{max}$ for a central portion 114A to a minimum electrode width $e_{min}$ for the end portions 114B and 114C which extend from central portion 114A toward the sides of passage 24. For example, the width $e_{min}$ can be chosen as only one quarter of the width of $e_{max}$ (e.g., without limitation, 0.5 mm and 2. mm respectively). As a result of such varied widths $e_{max}$ and $e_{min}$, the trailing edge (i.e., the edge of electrode 114 disposed furthest from inlet 26 of passage 24, not numbered in FIG. 9) of central portion 114 is offset a predetermined distance $d_2$ from the trailing edges (not numbered) of the outer portions 114B and 114C of each electrode 114, while the leading edge (i.e., the edge of the particular electrode 114 disposed closest to inlet 26 of passage 24) is generally constant along the entire length of each electrode 114. Such dimensioning of each electrode is provided in order to assist in forming the desired wave-like pattern in pumping membrane 38. By having a constant leading edge, pumping membrane 38 is initially attracted (either upward or downward depending on the electrode) toward a respective electrode 114 across generally the entire width $w_p$ of passage 24 (with the portions of membrane closest to outer portions 114B and 114C of electrode 114 initiating the movement), thus creating an initial "wave-front". The middle (i.e., the portion closest to central longitudinal axis A) of the "wave" is then further attracted to the wider (longer in the direction of the wave propagation) central portion 114A of electrode 114 which thus acts to propagate the wave-front generally away from inlet 26 and toward outlet 28 of passage 24.

Figure 10:
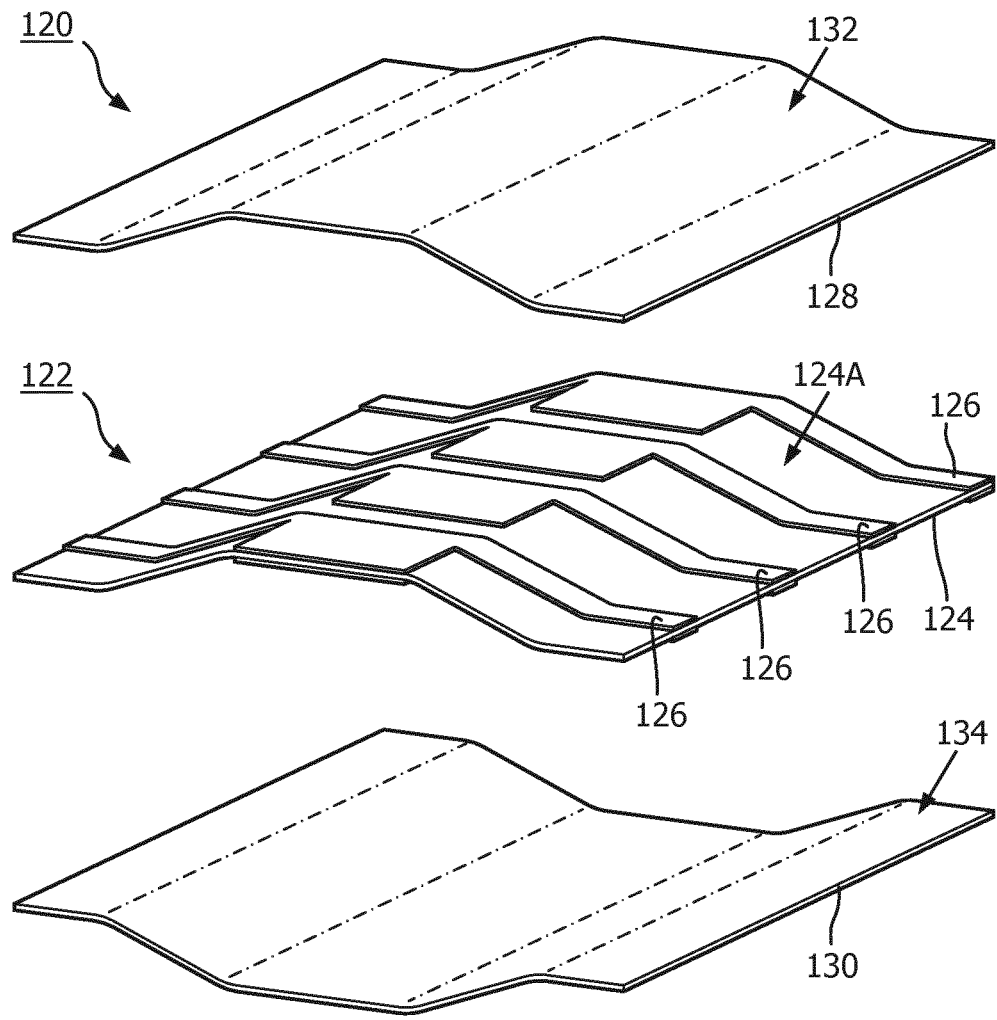
FIG. 10 is a partially exploded isometric view of a pumping apparatus according to another example embodiment of the invention.

As an alternative to using patterned electrodes on upper and lower portions of the frame, a patterned pumping membrane may be employed which is selectively attracted to unpatterned metal layers in the upper and lower portions of the frame which generally extend along the entire length L of passage 24. FIG. 10 shows a partially exploded isometric view of an example apparatus 120 according to an embodiment of the present invention which employs such a flexible patterned pumping membrane 122 (shown disposed in an upwardly arched position). Similar to the arrangement shown in FIG. 7, pumping membrane 122 includes a dielectric film 124, but instead of having a metal film, pumping membrane includes a plurality (four are shown) of electrodes 126 disposed on an upper surface 124A of dielectric film 124. Each of electrodes 126 are of a similar arrangement as electrodes 114 previously discussed in regard to FIG. 9. Also like the arrangement shown in FIG. 7, the upper and lower portions (not numbered) are formed from structural films 128, 130 which are coated on upper surfaces (not numbered) thereof with metal layers 132 and 134, respectively. Such arrangement of electrodes 126 functions in generally the same manner as the arrangement shown in FIG. 9.

Figure 11:
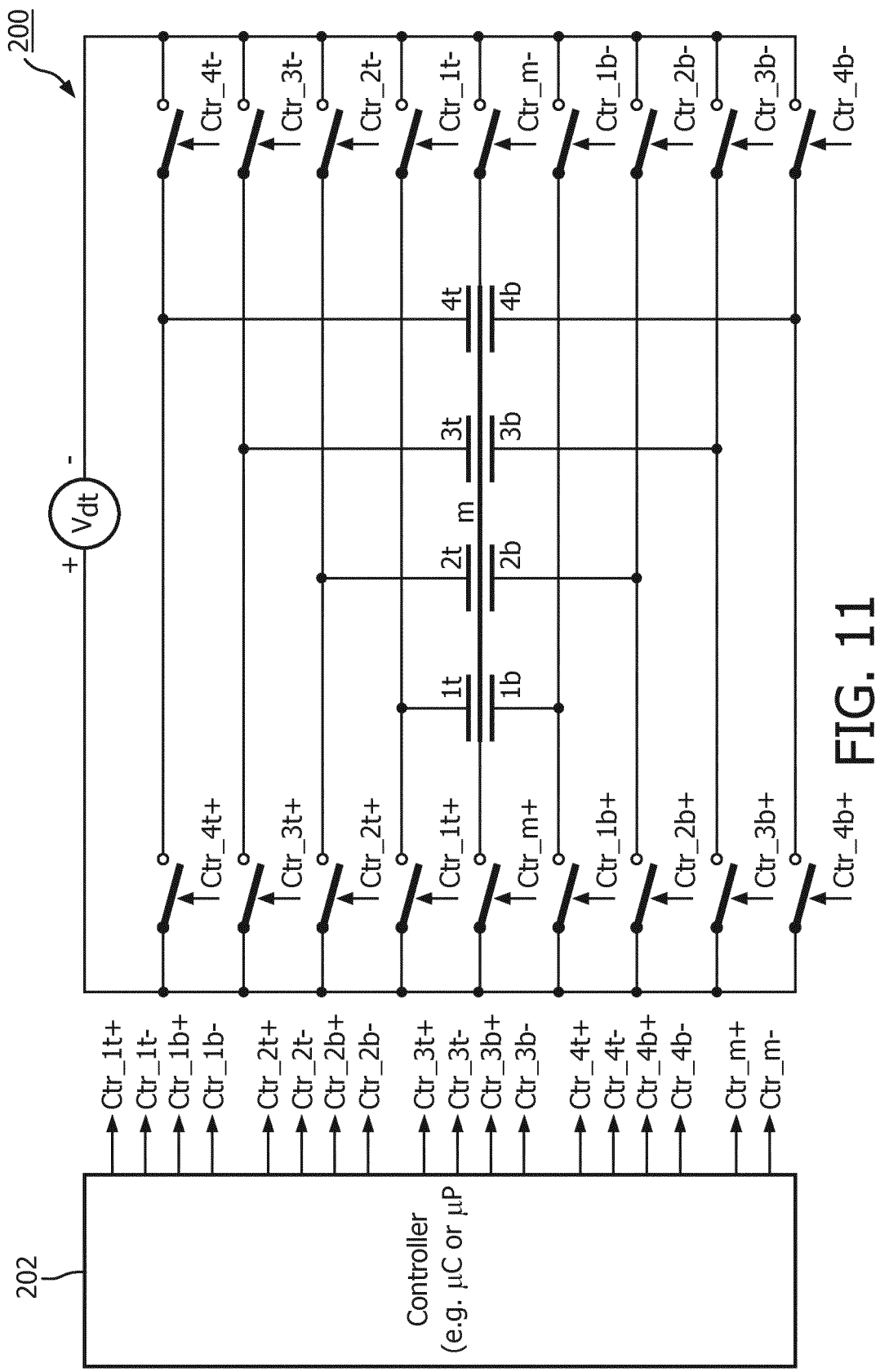
FIG. 11 is a schematic diagram showing an example arrangement of components of an electrical actuating system according to one example embodiment of the invention.

Having thus described a number of embodiments of example apparatuses and portions thereof an example arrangement, and operation thereof, of components of an electrical actuating system 200 according to one example embodiment of the invention will now be described in conjunction with FIGS. 11 and 12. FIG. 11 shows schematically the general arrangements of electrical components for use with an example arrangement such as previously described in FIG. 9. Accordingly, system 200 includes four top electrodes 1t, 2t, 3t, 4t (collectively referred to hereinafter as top electrodes xt), as well as four bottom electrodes 1b, 2b, 3b, 4b (collectively referred to hereinafter as bottom electrodes xb), with electrodes 1t and 1b being disposed closest to the inlet of the passage (such as shown in the left portion of FIG. 12) and electrodes 4t and 4b being disposed closest to the outlet of the passage (see FIG. 12). The pumping membrane which is disposed in the example passage includes a conductive metal layer m. As shown in FIG. 11, each of top electrodes xt are selectively electrically connected to a source of DC voltage $V_{dc}$ by a pair of switches Ctr_xt+ (wherein x indicates the particular electrode number) and Ctr_xt− (wherein x indicates the particular electrode number) such that either a positive voltage or a negative voltage may be selectively applied (i.e., by closing the particular aforementioned switch) to each of top electrodes xt. Similarly, each of bottom electrodes xb are selectively electrically connected to the source of DC voltage $V_{dc}$ by a pair of switches Ctr_xb+ (wherein x indicates the particular electrode number) and Ctr_xt− (wherein x indicates the particular electrode number) such that either a positive voltage or a negative voltage may be selectively applied (i.e., by closing the particular aforementioned switch) to each of bottom electrodes xb. The conductive metal layer is likewise selectively electrically connected to the source of DC voltage $V_{dc}$ by a pair of switches Ctr_m+ and Ctr_m− such that either a positive or negative voltage may be applied to the metal layer of the pumping membrane. Each of switches Ctr_xt+, Ctr_xt−, Ctr_xb+, Ctr_xb−, Ctr_m+ and Ctr_m− are controlled by a controller 202 which is connected to each switch via an optocoupler or other suitable arrangement. In order to induce electrostatic attraction among differently charged components, DC voltage source $V_{dc}$ produces a voltage in the range of about 200V-600V, depending on the particular application.

Figure 12:
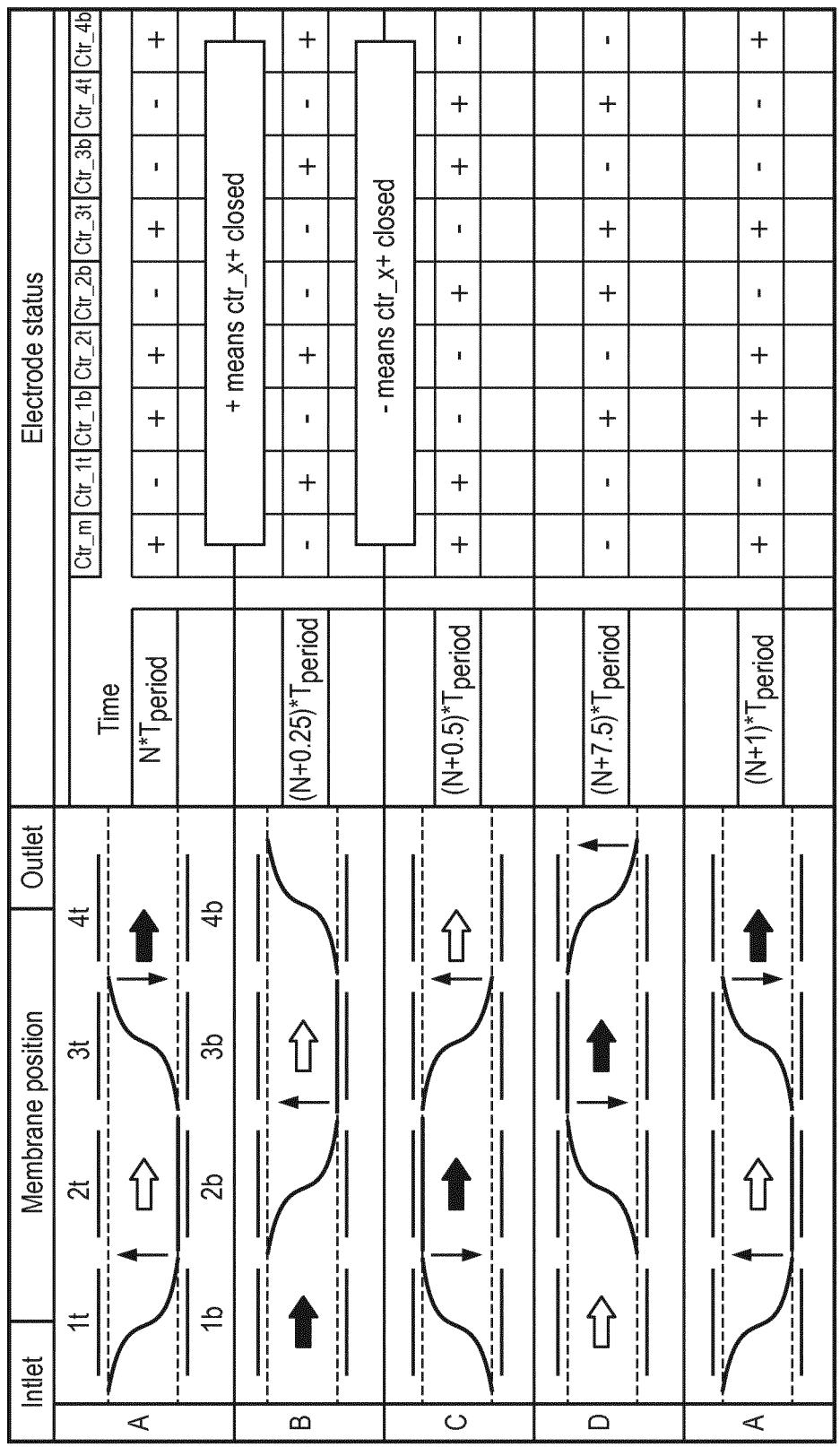
FIG. 12 is a chart showing an example switching sequence and corresponding membrane positioning in according to one example embodiment of the invention referring to the electrical actuating system of FIG. 11.

As generally shown in FIG. 12, by selectively independently applying (via controller 202 of FIG. 11) either positive or negative voltages to top and bottom electrodes xt and xb as well as to conductive layer m of the pumping membrane, the wave-like motion previously discussed in conjunction with FIGS. 4A and 4B can be produced. It is to be appreciated that potential build-up of residual charges on any of electrodes xt, xb or layer m can be reduced/eliminated by regularly reversing the polarity of the voltage applied to conductive layer m of the pumping membrane. It is also to be appreciated from the example arrangement of FIGS. 11 and 12 that peristaltic movement of fluid (e.g., air), as shown by the horizontal arrows in FIG. 12, can be accomplished with utilizing a minimal number (i.e., only four pairs) of spaced electrodes xt and xb. An even smaller number of pairs (e.g., one) may also be employed in instances where specialized electrode shapes are utilized (e.g., without limitation, an exaggerated, "stretched" version of an electrode such as 114 previously discussed) but will generally be less optimal.

FIGS. 13 and 14 show example switching sequences according to example embodiments of the invention for an apparatus such as shown in FIG. 10 utilizing an electrical arrangement and components similar to that described in conjunction with FIG. 11 which have been generally changed/adapted for switching the plurality of electrodes 126 which are part of pumping membrane 122 instead a plurality of electrodes in the top and bottom of the passage.

Figure 15:
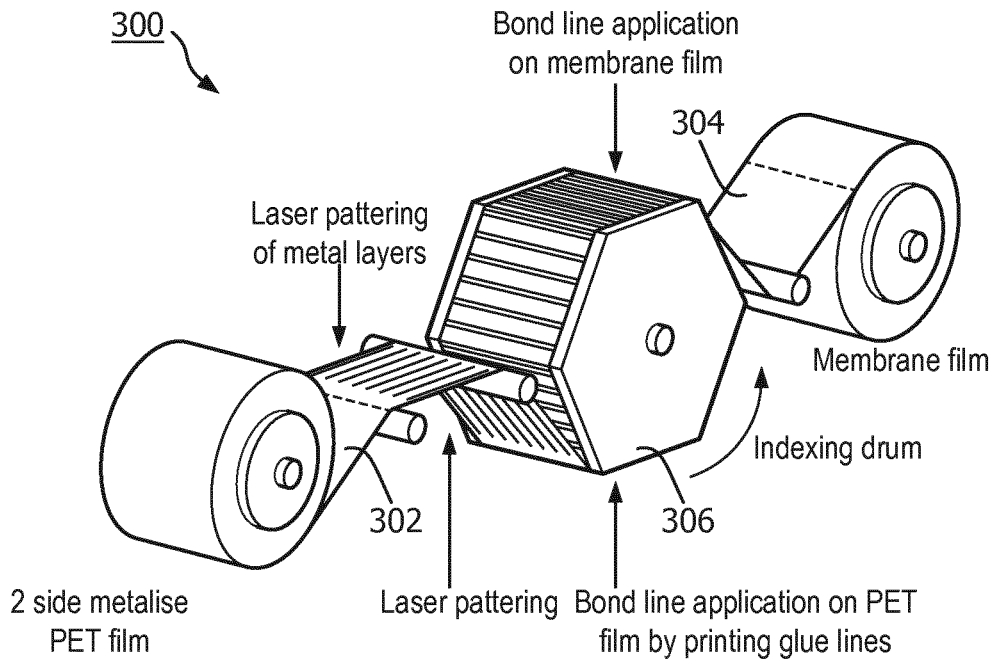
FIG. 15 shows an example arrangement for use in manufacturing apparatuses according to an example embodiment of the invention.

Having thus discussed example embodiments of the invention and example methods of operating, a discussion of a method of manufacture in accordance with an example embodiment of the invention will now be discussed. For applications using a pumping apparatus, such as pumping apparatus 20 with a channel 24 previously described in conjunction with FIGS. 2 and 3 herein, which require flow rates far beyond the range of micro-fluids, a combination of many passages 24 would be needed (for example, without limitation, 20 parallel passages stacked 250 times producing an array of 5,000 passages and related components would generally suffice for a typical CPAP application). An arrangement 300 for carrying out an efficient production method for use in manufacturing such a combination is shown generally in FIG. 15. In such method, the combination of structural films, along with metal layers and/or dielectric layers disposed thereon (such as previously discussed in regard to FIGS. 6-10 herein) which is generally indicated by 302, as well as pumping membrane film (including any subcomponents thereof, such as also previously discussed in regard to FIGS. 6-10 herein) which is generally indicated by 304 is wound around an indexing drum 306 while applying glue at the positions where the structural film 302 and pumping membrane film 304 are desired to be contacting and secured together in the expanded final configuration, such as shown generally at the areas indicated with an X in the example arrangement of FIGS. 6 and 16 herein. The laser patterning processes shown in FIG. 15 allow the patterning of the metal layers on two sides of the structure forming film 302.

Figure 16:
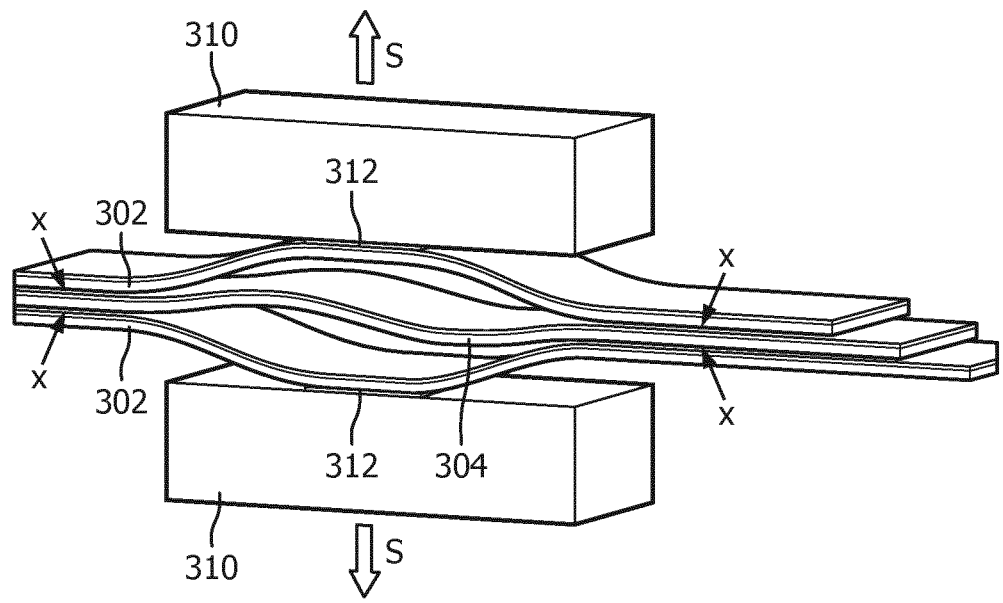
FIG. 16 shows a further example arrangement for use in manufacturing apparatuses according to an example embodiment of the invention.

After cutting loose the stacked combination of structural films 302 and pumping membrane films 304 from the rotated drum 306, the layered structure can be stretched by applying a force S in the thickness direction of the pump apparatus to generally expand the height of each passage from generally zero to a predetermined value and thus form the honeycomb structure with the integrated pumping membrane, such as generally shown in the example arrangement of FIG. 16 which shows such stretching for a single passage arrangement. In such arrangement, the structure being stretched may be temporarily bonded to a stretching apparatus 310 via a suitable temporary bonding material 312 (e.g., without limitation, glue, thermal bonding, etc.).

Figure 17:
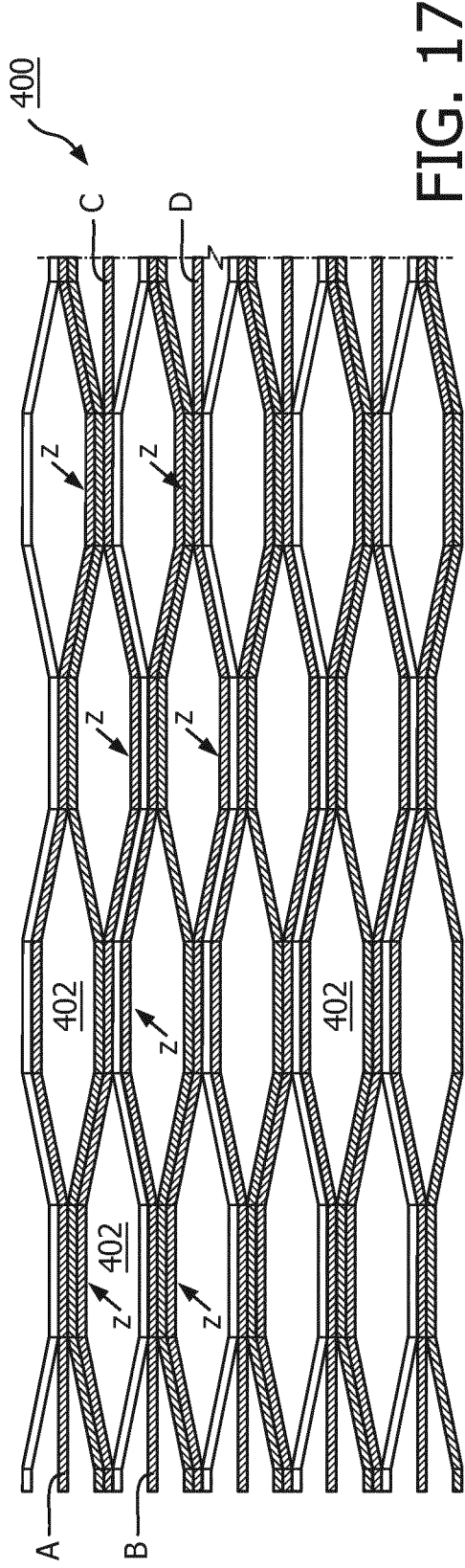
FIGS. 17-20 show example arrangements of an interconnect structure according to an example embodiment of the invention.

Another important step in the manufacturing process is connecting all the common electrodes and/or conductive layers from each of the individual passages together and making electrical connections to the outside world. FIGS. 17-20 provide a solution as to how such connections may be accomplished in accordance with an example embodiment of the present invention. Referring first to FIG. 17, an end view (i.e., looking through the passages) of a portion of an example array 400 of passages 402 (only three are labeled) is shown. In such arrangement, the pumping membranes (not numbered) of some of passages 402 have been bonded to either the upper structural film or the lower structural film in a predetermined patter via a suitable bonding material. The passages in which the pumping membranes have been bonded are previously designed so as to have a particular conductive element (e.g., a metal layer, an electrode layer, a conductive layer of a pumping membrane, etc.) exposed therein when the pumping membrane is bonded to either the upper or lower structural film. The bonded areas for the four uppermost pumping membranes A, B, C and D are indicated generally at Z. Such bonding is carried out during a manufacturing process such as previously discussed in conjunction with FIGS. 15 and 16.

Figure 18:
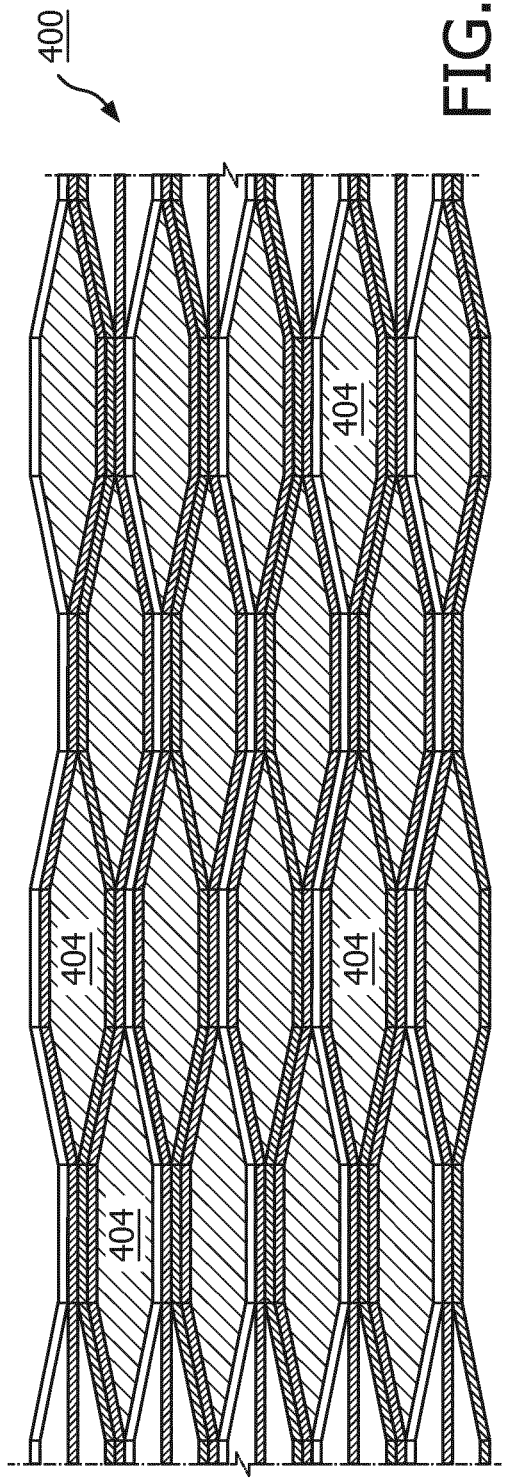
Figure 19:
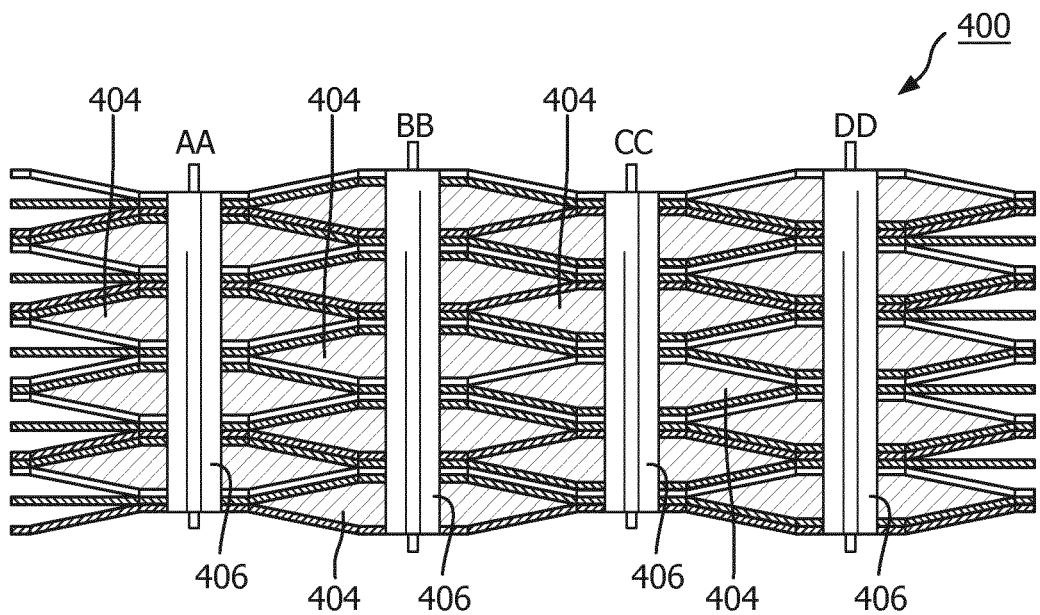
Figure 20:
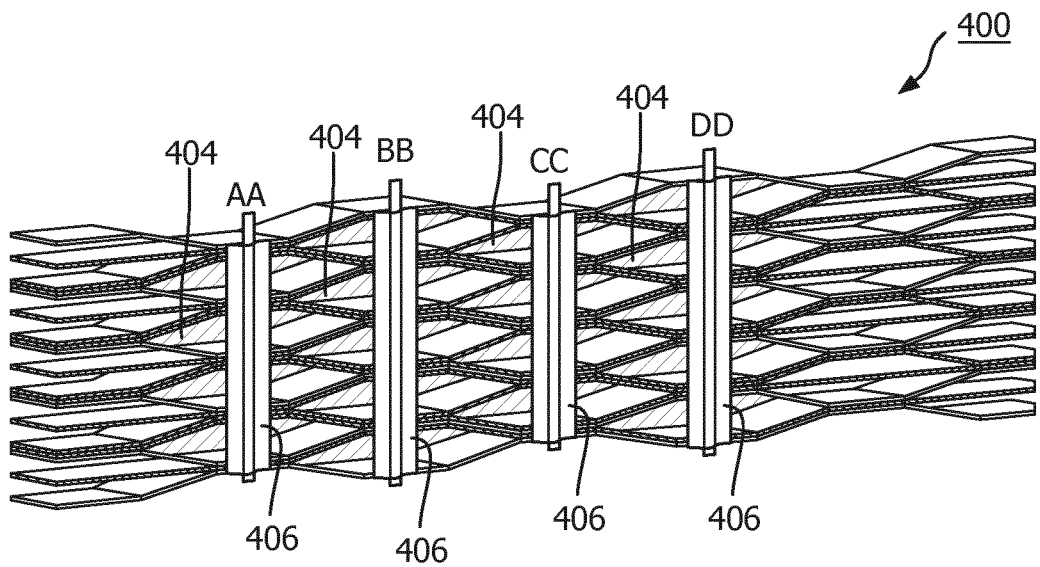

After the pumping membranes have been bonded, a conductive ink 404, or other suitable conductive material, is selectively disposed (e.g., without limitation, by capillary means) in the passages in which the pumping membranes were previously bonded, such as shown in FIG. 18. It is to be appreciated that as a result of the layered structure of the array 400, all of the conductors needed for a row of 20 passages could be addressed with only a few of such filled passages.

After the conductive ink 404 has been disposed in the selected passages, a rigid vertical conductor 406 is electrically connected via a suitable process (e.g, without limitation, soldering) to each of the filled passages in a vertical stack, thus electrically interconnecting the common electrical elements in each row of the array and providing a rigid connection point for connection of further electrical connections AA, BB, CC, DD to the outside world.

In summary, it is to be appreciated that embodiments of the invention provide an apparatus that for use in producing a flow of a fluid (e.g., without limitation, a gas) which can be readily sized for a given application by varying, without limitation, one or more of the width, height, length, quantity of electrodes, and electrode geometry of a particular passage. Additionally or alternatively, the quantity of passages employed in an apparatus can be readily varied to meet the requirements of a particular application.

It is also to be appreciated that embodiments of the invention may be arranged so as to be operated bi-directionally. For example, without limitation, such feature may be employed in embodiments wherein such an apparatus is employed to support breathing (i.e., inhaling/exhaling) through a mask with a filter. It is also to be appreciated that as an alternative to being used as a pumping apparatus for producing a desired flow of a fluid, embodiments of the invention may also be employed to create a vacuum (e.g., employed as a vacuum pump). It is also to be appreciated that embodiments of the invention may be employed in non-pumping applications. For example, without limitation, embodiments of the invention may be employed to act as a valve for blocking the flow of a fluid by effectively "freezing" the pumping membrane or membranes of an apparatus in a predetermined waveform which blocks the associated passage or passages. Such approach may similarly be used as an optical device which either allows light to pass through (e.g., by having the pumping membrane(s) disposed against the top of bottom of the passage(s)) or be blocked (e.g., by having the pumping membrane(s) disposed blocking the passage(s)).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. As another example, it is to be appreciated that one or more of the quantity, sizing, spacing, positioning, etc. of electrodes utilized within a passage or between multiple passages in embodiments of the invention may be varied without varying from the scope of the invention. It is also to be appreciated that the relative positioning lengthwise (i.e., positioning between the inlet and the out) from one passage to another of elements may be varied (e.g., without limitation to create offsetting waveforms in the pumping membranes) without varying from the scope of the invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A method of producing a flow of a fluid through a passage defined in a rigid frame, the method comprising:
   selectively actuating a flexible membrane disposed across a midpoint of the passage with an actuating system in a manner which produces a wave-like motion in the membrane thereby causing a peristaltic movement of the fluid through the passage, wherein the flexible membrane comprises a membrane electrode arrangement, wherein the actuating system comprises:
   an upper electrode arrangement disposed adjacent the upper portion of the passage; and
   a lower electrode arrangement disposed adjacent the lower portion of the passage;
   and wherein:
   the membrane electrode arrangement comprises a number of membrane electrodes each comprising a central portion and an end portion, wherein the width of the end portion is less than or equal to a half of the width of the central portion; or
   the upper electrode arrangement comprises a number of upper electrodes and the lower electrode arrangement comprises a number of lower electrodes, wherein the plurality of upper electrodes and the plurality of lower electrodes each comprise a central portion and an end portion, wherein the width of the end portion is less than or equal to a half of the width of the central portion, wherein the method further comprises selectively electrically connecting the membrane electrode arrangement, the upper electrode arrangement, and the lower electrode arrangement.

2. The method of claim 1, wherein selectively actuating the membrane comprises moving portions of the membrane in a direction perpendicular to a longitudinal central axis of the passage.

3. The method of claim 1, wherein the membrane comprises a conductive material; and
   wherein selectively actuating the membrane comprises attracting portions of the membrane toward one of an upper portion of the passage or toward a lower portion of the passage via an electrostatic force.

4. The method of claim 1, wherein:
   the actuating system comprises: the number of upper electrodes disposed adjacent an upper portion of the passage; the number of lower electrodes disposed adjacent a lower portion of the passage; and wherein the number of membrane electrodes comprises a single membrane electrode disposed in or on the membrane; and
   selectively actuating the membrane comprises attracting portions of the membrane toward either the upper portion of the passage or toward the lower portion of the passage via an electrostatic force by:
   electrically connecting the single membrane electrode to ground;
   selectively electrically connecting an upper electrode of the number of upper electrodes to a positive voltage; and
   selectively electrically connecting a lower electrode of the number of lower electrodes to a negative voltage.

5. The method of claim 1, wherein:
   the actuating system comprises: the number of upper electrodes disposed adjacent an upper portion of the passage; the number of lower electrodes disposed adjacent a lower portion of the passage; and the number of membrane electrodes disposed in or on the membrane; and
   selectively actuating the membrane comprises attracting portions of the membrane toward either the upper portion of the passage or toward the lower portion of the passage via an electrostatic force by:
   selectively electrically connecting the number of membrane electrodes to either a positive voltage or a negative voltage;
   selectively electrically connecting at least one of the number of upper electrodes to a positive voltage; and
   selectively electrically connecting at least one of the number of lower electrodes to a negative voltage.

6. The method of claim 1,
   wherein the number of upper electrodes comprises a plurality of upper electrodes disposed adjacent an upper portion of the passage; wherein the number of lower electrodes comprises a plurality of lower electrodes disposed adjacent a lower portion of the passage; and wherein the number of membrane electrodes comprises a single membrane electrode disposed in or on the membrane; and
   selectively actuating the membrane comprises attracting portions of the membrane toward either the upper portion of the passage or toward the lower portion of the passage via an electrostatic force by:
   electrically connecting the single membrane electrode to ground;
   selectively electrically connecting at least one of the plurality of upper electrodes to a positive voltage; and
   selectively electrically connecting at least one of the plurality of lower electrodes to a negative voltage.

7. The method of claim 6, wherein selectively actuating the membrane further comprises:
   selectively electrically connecting at least another one of the plurality of upper electrodes to a negative voltage; and
   selectively electrically connecting at least another one of the plurality of lower electrodes to a positive voltage.

8. The method of claim 1,
   wherein the number of upper electrodes comprises a plurality of upper electrodes disposed adjacent an upper portion of the passage; wherein the number of lower electrodes comprises a plurality of lower electrodes disposed adjacent a lower portion of the passage; and wherein the number of membrane electrodes comprises a single membrane electrode disposed in or on the membrane; and
   selectively actuating the membrane comprises attracting portions of the membrane toward either the upper portion of the passage or toward the lower portion of
the passage via an electrostatic force by:
  selectively electrically connecting the single membrane
    electrode to either a positive voltage or a negative
    voltage;
  selectively electrically connecting at least one of the
    plurality of upper electrodes to a positive voltage;
    and
  selectively electrically connecting at least one of the
    plurality of lower electrodes to a negative voltage.

9. The method of claim 8, wherein selectively actuating the membrane further comprises:
  selectively electrically connecting at least another one of
    the plurality of upper electrodes to a negative voltage;
    and
  selectively electrically connecting at least another one of
    the plurality of lower electrodes to a positive voltage.

10. The method of claim 1,
  wherein the number of upper electrodes comprises a single upper electrode disposed adjacent an upper portion of the passage; wherein the number of lower electrodes comprises a single lower electrode disposed adjacent a lower portion of the passage; and when the number of membrane electrodes comprises a plurality of membrane electrodes disposed in or on the membrane; and
  selectively actuating the membrane comprises attracting portions of the membrane toward either the upper portion of the passage or toward the lower portion of the passage via an electrostatic force by:
    selectively electrically connecting at least one of the plurality of membrane electrodes to a positive voltage;
    selectively electrically connecting the single upper electrode to one selected from the group consisting of a positive voltage and a negative voltage; and
    selectively electrically connecting the single lower electrode to the other one in the group.

11. The method of claim 10, wherein selectively actuating the membrane further comprises selectively electrically coupling another one of the plurality of membrane electrodes to a negative voltage.

12. The method of claim 1,
  wherein the number of upper electrodes disposed adjacent an upper portion of the passage; the number of lower electrodes disposed adjacent a lower portion of the passage; and wherein the number of membrane electrodes comprises a single membrane electrode disposed in or on the membrane; and
  selectively actuating the membrane comprises attracting portions of the membrane toward either the upper portion of the passage or toward the lower portion of the passage via an electrostatic force by:
    electrically connecting the single membrane electrode to a first potential;
    electrically connecting at least one of an upper electrode of the number of upper electrodes or a lower electrode of the number of lower electrodes to a second potential different than the first potential.

13. The method of claim 1,
  wherein the number of upper electrodes comprises a single upper electrode disposed adjacent an upper portion of the passage; wherein the number of lower electrodes comprises a single lower electrode disposed adjacent a lower portion of the passage; and wherein the number of membrane electrodes comprises a plurality of membrane electrodes disposed in or on the membrane; and
  selectively actuating the membrane comprises attracting portions of the membrane toward either the upper portion of the passage or toward the lower portion of the passage via an electrostatic force by:
    electrically connecting the single upper electrode to a first potential;
    electrically connecting the single lower electrode to a second potential different than the first potential; and
    electrically connecting at least one of the plurality of membrane electrodes to a third potential different from at least one of the first potential and the second potential.

14. The method of claim 13, wherein selectively actuating the membrane further comprises electrically connecting at least another one of the plurality of membrane electrodes to a fourth potential different from at least one of the first potential and the second potential.

15. A system for producing a flow of a fluid through a passage defined in a rigid frame, wherein the passage comprises an upper portion and a lower portion, the system comprising:
  a flexible membrane disposed across a midpoint of the passage, wherein the flexible membrane comprises a membrane electrode arrangement;
  an actuating system adapted to selectively actuate the flexible membrane in a manner which produces a wave-like motion in the membrane thereby causing a peristaltic movement of the fluid through the passage, wherein the actuating system comprises:
    an upper electrode arrangement disposed adjacent the upper portion of the passage; and
    a lower electrode arrangement disposed adjacent the lower portion of the passage;
  and wherein:
    the membrane electrode arrangement comprises a number of membrane electrodes each comprising a central portion and an end portion, wherein the width of the end portion is less than or equal to a half of the width of the central portion; or
    the upper electrode arrangement comprises a number of upper electrodes and the lower electrode arrangement comprises a number of lower electrodes, wherein the number of upper electrodes and the number of lower electrodes each comprise a central portion and an end portion, wherein the width of the end portion is less than or equal to a half of the width of the central portion.

16. The method of claim 1, further wherein the width of the end portion of a respective membrane electrode is less than or equal to a quarter of the width of the central portion of the respective membrane electrode, or further wherein the width of the end portion of a respective upper or lower electrode is less than or equal to a quarter of the width of the central portion of the respective upper or lower electrode.

17. The system of claim 15, further wherein the width of the end portion of a respective membrane electrode is less than or equal to a quarter of the width of the central portion of the respective membrane electrode, or further wherein the width of the end portion of a respective upper or lower electrode is less than or equal to a quarter of the width of the central portion of the respective upper or lower electrode.

18. The system of claim 15, wherein the number of membrane electrodes comprises a plurality of membrane electrodes disposed in or on the membrane, wherein the number of upper electrodes comprises a plurality of upper electrodes disposed adjacent an upper portion of the passage, and wherein the number of lower electrodes comprises a plurality of lower electrodes disposed adjacent a lower portion of the passage.

19. The system of claim 15, wherein the number of membrane electrodes comprises a single membrane electrode disposed in or on the membrane, wherein the number of upper electrodes comprises a plurality of upper electrodes disposed adjacent an upper portion of the passage, and wherein the number of lower electrodes comprises a plurality of lower electrodes disposed adjacent a lower portion of the passage.

20. The system of claim 15, wherein the number of membrane electrodes comprises a plurality of membrane electrodes disposed in or on the membrane, wherein the number of upper electrodes comprises a single upper electrode disposed adjacent an upper portion of the passage, and wherein the number of lower electrodes comprises a single lower electrode disposed adjacent a lower portion of the passage.

* * * * *